(12) United States Patent
Friedman et al.

(10) Patent No.: US 12,311,025 B2
(45) Date of Patent: May 27, 2025

(54) FORMULATIONS FOR EYE TREATMENTS

(71) Applicant: Avedro, Inc., Burlington, MA (US)

(72) Inventors: Marc D. Friedman, Needham, MA (US); Pavel Kamaev, Lexington, MA (US); Martin Joseph Coffey, Buffalo Grove, IL (US); Rajesh K. Rajpal, McLean, VA (US); Alexandra Nicklin, Cambridge, MA (US)

(73) Assignee: Avedro, Inc., Burlington, MA (US)

( * ) Notice: Subject to any disclaimer, the term of this patent is extended or adjusted under 35 U.S.C. 154(b) by 0 days.

(21) Appl. No.: 16/933,059

(22) Filed: Jul. 20, 2020

(65) Prior Publication Data

US 2020/0345847 A1   Nov. 5, 2020

Related U.S. Application Data

(63) Continuation of application No. 15/901,496, filed on Feb. 21, 2018, now abandoned.

(60) Provisional application No. 62/461,591, filed on Feb. 21, 2017.

(51) Int. Cl.
| | |
|---|---|
| A61K 41/00 | (2020.01) |
| A61F 9/007 | (2006.01) |
| A61K 9/00 | (2006.01) |
| A61K 47/18 | (2017.01) |
| A61N 5/06 | (2006.01) |
| A61P 27/02 | (2006.01) |

(52) U.S. Cl.
CPC ........ *A61K 41/0057* (2013.01); *A61F 9/0079* (2013.01); *A61K 9/0048* (2013.01); *A61K 47/186* (2013.01); *A61N 5/062* (2013.01); *A61P 27/02* (2018.01); *A61N 2005/0661* (2013.01)

(58) Field of Classification Search
CPC .............. A61K 41/0057; A61K 9/0048; A61K 47/186; A61F 9/0079; A61N 5/062; A61N 2005/0661; A61P 27/02
See application file for complete search history.

(56) References Cited

U.S. PATENT DOCUMENTS

| | | | | |
|---|---|---|---|---|
| 6,511,660 B1 * | 1/2003 | Lin | ...................... | A61K 9/0048 424/78.04 |
| 8,574,277 B2 * | 11/2013 | Muller | ................... | A61N 5/062 606/4 |
| 9,707,126 B2 * | 7/2017 | Friedman | ................ | A61P 27/10 |
| 11,207,410 B2 * | 12/2021 | Kamaev | ................... | A61P 43/00 |
| 2003/0056281 A1 * | 3/2003 | Hasegawa | .............. | A61N 2/002 2/206 |
| 2011/0280763 A1 | 11/2011 | Trokel et al. | | |
| 2012/0121567 A1 ‡ | 5/2012 | Troisi | ................... | A61K 31/203 424/94.1 |
| 2012/0203161 A1 * | 8/2012 | Herekar | .................. | A61P 27/02 604/20 |
| 2013/0060187 A1 * | 3/2013 | Friedman | ............. | A61F 9/0079 604/20 |
| 2014/0371123 A1 ‡ | 12/2014 | Nakata | ................... | A61K 31/07 510/112 |
| 2015/0174105 A1 * | 6/2015 | Hernandez | ........... | A61K 9/0048 514/397 |

FOREIGN PATENT DOCUMENTS

| | | | |
|---|---|---|---|
| WO | WO 2010023705 A1 ‡ | 3/2010 | |
| WO | 2011/019940 A2 | 2/2011 | |
| WO | WO 2011012557 A1 ‡ | 2/2011 | |

OTHER PUBLICATIONS

Saettone et al (Semisolid ophthalmic vehicles. III. An evaluation of four organic hydrogels containing pilocarpine). International Journal of Pharmaceutics, 31 (1986) 261-270. (Year: 1986).*
Hillman (Management of acute glaucoma with pilocarpine-soaked hydrophilic lens). Brit. J. Ophthal. (1974) 58, 674. (Year: 1974).*
Kissner et al (Pharmacological Modification of the Epithelial Permeability by Benzalkonium Chloride in UVA/Riboflavin Corneal Collagen Cross-Linking), Current eye research, 35(8), 715-721, 2010 (Year: 2010).*
Nguyen et al (Review of hydroxypropyl cellulose ophthalmic inserts for treatment of dry eye), Clinical Opththamology, Dovepress 2011:5 587-591. (Year: 2011).*
International Search Report issued in co-pending International Patent Application No. PCT/US2018,018970, ISA/RU, dated May 17, 2018, 4 pages.‡

(Continued)

*Primary Examiner* — Mina Haghighatian
(74) *Attorney, Agent, or Firm* — K&L Gates LLP (57) ABSTRACT

Formulations, are used for eye treatments, e.g., cross-linking treatments. For example, a therapeutic formulation includes a photosensitizer and delivery agent(s), wherein the delivery agent(s) include at least one of: anesthetic agent(s), analgesic agent(s), tonicity agent(s), or shear-thinning, or viscosity-increasing agent(s). In another example, a method includes applying preparatory formulation(s) to increase a permeability of a corneal epithelium, and applying therapeutic formulation(s) to the epithelium, where the preparatory formulation(s) include zinc metalloproteinase, copper metalloproteinase, papain, bromelain, actinidin, ficain, N-acetylcysteine, ambroxol, carbocisteine, and/or erdosteine. In yet another example, a method includes applying therapeutic formulation(s) to a corneal epithelium to deliver the therapeutic formulation(s) to a stroma, and applying enhancement formulation(s) to the epithelium in response to applying the therapeutic formulation(s), where: the enhancement formulation(s) remove the therapeutic formulation(s) from the epithelium; close tight junctions of the epithelium; promote oxidation for the therapeutic agent(s); and/or further deliver the therapeutic formulation(s) to the stroma.

18 Claims, 4 Drawing Sheets

(56) References Cited

OTHER PUBLICATIONS

Written Opinion issued in co-pending International Patent Application No. PCT/US2018/018970, ISA/RU, dated May 17, 2018, 5 pages.‡

Loginov, G.N., Features of Therapeutic Interventions During Post-surgical Period of Cornea Crosslinking, Modern Technologies in Opthalmology, No. 4, 2014, pp. 48-50.‡

Stojanovic, Aleksandar et al., "Safety and Efficacy of Epithelium-On Corneal Collagen Cross-Linking Using a Multifactorial Approach to Achieve Proper Stomal Riboflavin Saturation," Journal of Ophthalmology, 2012, Article ID 498435, 8 pages, paragraph 2.1.

Extended European Search Report issued Feb. 12, 2020 for European Patent Application No. 18756993.4.

Leonard, "The Epic Future of Epi-on", https://www.reviewofophthalmology.com/article/the-epic-future-of-epion, Published on Oct. 10, 2021, in 14 pages.

\* cited by examiner
‡ imported from a related application

FORMULATIONS FOR EYE TREATMENTS

CROSS-REFERENCE TO RELATED APPLICATIONS

This application is a continuation of U.S. patent application Ser. No. 15/901,496, filed Feb. 21, 2018, which claims the benefit of, and priority to, U.S. Provisional Patent Application Ser. No. 62/461,591, filed Feb. 21, 2017, the contents of these applications being incorporated entirely herein by reference.

BACKGROUND

Field

The present disclosure pertains to treatments for disorders of the eye, and more particularly, to the use of formulations, e.g., preparation solutions, photosensitizer formulations, rinse solutions, etc., for eye treatments, e.g., cross-linking treatments.

Description of Related Art

Certain photosensitizers may be applied to the eye for eye treatments. For example, photosensitizers can generate cross-linking activity in the cornea. Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed to induce refractive changes in the cornea to correct disorders such as myopia, hyperopia, myopia, hyperopia, astigmatism, irregular astigmatism, presbyopia, etc.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

SUMMARY

Embodiments according to the present disclosure relate to the use of formulations, e.g., preparation solutions, photosensitizer formulations, rinse solutions, etc., for eye treatments, e.g., cross-linking treatments.

According to an example embodiment, a therapeutic formulation for treating an eye includes a photosensitizer and one or more delivery agents. The one or more delivery agents include at least one of: one or more anesthetic agents, one or more analgesic agents, one or more tonicity agents, or one or more shear-thinning, viscosity-increasing agents. The one or more anesthetic agents may include pilocarpine, proparacaine, tetracaine, or oxybuprocaine. The one or more analgesic agents may include at least one of menthol, benzyl alcohol, or phenylethyl alcohol. The one or more tonicity agents may include at least one of glycerin, propylene glycol, polyethylene glycol (PEG)-8, ethanol, benzyl alcohol, phenylethyl alcohol, or triacetin. The one or more shear-thinning, viscosity-increasing agents may include at least one of carbomer, polycarbophil, gellan gum, xanthan gum, carboxymethyl cellulose sodium, or sodium hyaluronate. The one or more delivery agents may further include one or more ionic surfactants, and the one or more ionic surfactants may include benzalkonium chloride. The one or more delivery agents may further include one or more non-ionic surfactants, and the one or more non-ionic surfactants may include at least one of poloxamer 407, tetronic 1107, tetronic 1304, polysorbate 80, polyethylene glycol (PEG)-40 hydrogenated castor oil, lecithin, polysorbate 60, polyethylene glycol (PEG)-35 castor oil, tocophersolan (TPGS), nonoxynol-9, or tyloxapol. The one or more delivery agents may further include one or more chelating agents, and the one or more chelating agents may include at least one of ethylenediaminetetraacetic acid (EDTA) or citrate.

According to another example embodiment, a method for treating an eye includes applying one or more preparatory formulations to an epithelium of a cornea. The one or more preparatory formulations increases a permeability of the epithelium of the cornea. The one or more preparatory formulations include at least one of: zinc metalloproteinase, copper metalloproteinase, papain, bromelain, actinidin, ficain, N-acetylcysteine, ambroxol, carbocisteine, or erdosteine. The method also includes applying one or more therapeutic formulations to the epithelium in response to the increased permeability of the epithelium. The one or more preparatory formulations may further include one or more anesthetic agents, and the one or more anesthetic agents may include at least one of pilocarpine, proparacaine, tetracaine, or oxybuprocaine.

According to yet another example embodiment, a method for treating an eye includes applying one or more therapeutic formulations to an epithelium of a cornea to deliver the one or more therapeutic formulations to a stroma of the cornea. The method includes applying one or more enhancement formulations to the epithelium in response to applying the one or more therapeutic formulations. The one or more enhancement formulations are configured to at least one of: (i) remove the one or more therapeutic formulations from the epithelium of the cornea without diluting the one or more therapeutic agents delivered to the stroma; (ii) close tight junctions of the epithelium to control hydration of the cornea; (iii) promote oxidation for the one or more therapeutic agents delivered to the stroma; or (iv) further deliver the one or more therapeutic formulations from the epithelium to the stroma. The one or more enhancement formulations may include at least one of one or more divalent metal salts, one or more pro-oxidants, or one or more glycosaminoglycans. The method may further include applying one or more post-treatment formulations in response to applying the one or more enhancement formulations, and the one or more post-treatment formulations may include at least one of one or more divalent metal salts, one or more viscosity agents, one or more glycosaminoglycans, or one or more antibiotics. The one or more therapeutic agents may include a photosensitizer, and the method may further include photoactivating the photosensitizer by delivering a dose of illumination to the cornea.

DETAILED DESCRIPTION

Figure 1:
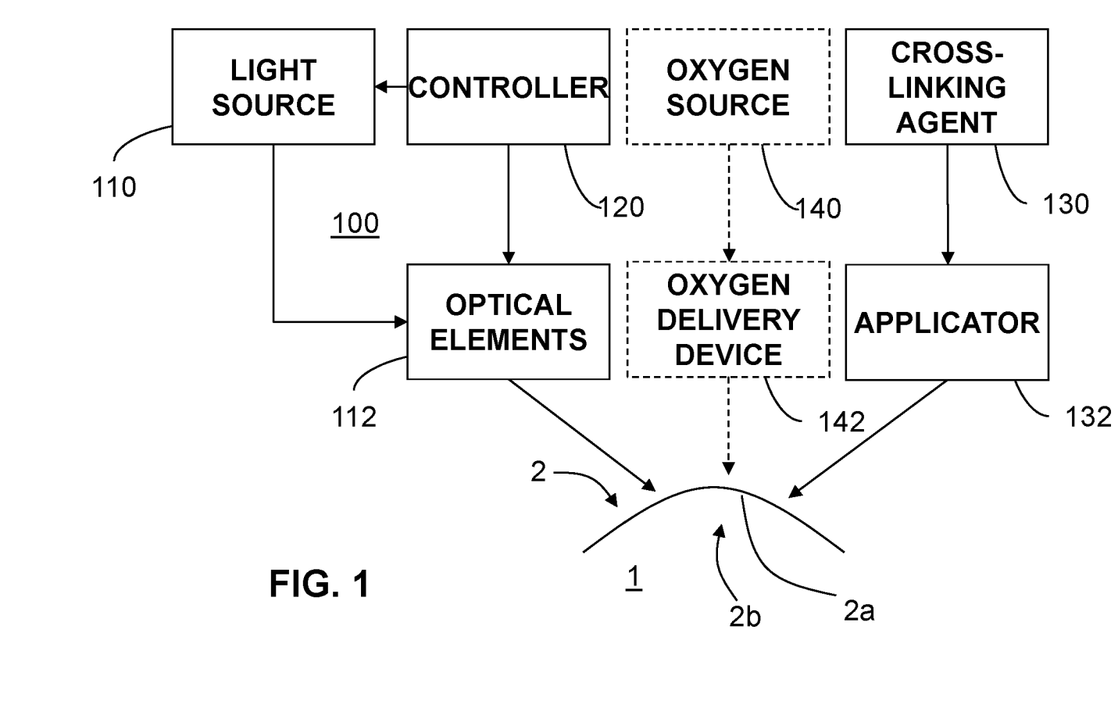
FIG. 1 illustrates an example system that delivers a cross-linking agent and photoactivating light to a cornea of an eye in order to generate cross-linking of corneal collagen, according to aspects of the present disclosure.

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. Example systems and methods for applying the cross-linking agent is described in U.S. Patent Application Publication No. 2017/0296383, filed Apr. 13, 2017 and titled "Systems and Methods for Delivering Drugs to an Eye," the contents of which are incorporated entirely herein by reference.

The cross-linking agent 130 may be provided in a formulation that allows the cross-linking agent 130 to pass through the corneal epithelium 2a and to underlying regions in the corneal stroma 2b. Alternatively, the corneal epithelium 2a may be removed or otherwise incised to allow the cross-linking agent 130 to be applied more directly to the underlying tissue.

The treatment system 100 includes an illumination system with a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm) light. Alternatively, the photoactivating light may include another wavelength, such as a visible wavelength (e.g., approximately 452 nm). As described further below, corneal cross-linking improves corneal strength by creating chemical bonds within the corneal tissue according to a system of photochemical kinetic reactions. For instance, riboflavin and the photoactivating light may be applied to stabilize and/or strengthen corneal tissue to address diseases such as keratoconus or post-LASIK ectasia.

The treatment system 100 includes one or more controllers 120 that control aspects of the system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photo-activating light to particular focal planes within the cornea 2, e.g., at a particular depths in the underlying region 2b where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 $mW/cm^2$, larger irradiance of the photoactivating light, e.g., multiples of 5 $mW/cm^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 $J/cm^2$, or as high as 20 $J/cm^2$ or 30 $J/cm^2$. The effective dose described can be delivered from a single application of energy, or from repeated applications of energy.

The optical elements 112 of the treatment system 100 may include a digital micro-mirror device (DMD) to modulate the application of photoactivating light spatially and temporally. Using DMD technology, the photoactivating light from the light source 110 is projected in a precise spatial pattern that is created by microscopically small mirrors laid out in a matrix on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Aspects of a dosimetry system are described in further detail below. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking.

When the cross-linking agent 130 is riboflavin in particular, the UVA light may be applied continuously (continuous wave (CW)) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 mW/cm$^2$ to approximately 1000 mW/cm$^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for instance, may involve combinations of myopia, hyperopia, astigmatism, irregular astigmatism, presbyopia and complex corneal refractive surface corrections because of ophthalmic conditions such as keratoconus, pellucid marginal disease, post-LASIK ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference.

The addition of oxygen also affects the amount of corneal stiffening. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference. Additionally, an example mask device for delivering concentrations of oxygen as well as photoactivating light in eye treatments is described in U.S. Patent Application Publication No. 2017/0156926, filed Dec. 3, 2016 and titled "Systems and Methods for Treating an Eye with a Mask Device," the contents of which are incorporated entirely herein by reference. For instance, a mask may be placed over the eye(s) to produce a consistent and known oxygen concentration above the surface.

When riboflavin absorbs radiant energy, especially light, it undergoes photoactivation. There are two photochemical kinetic pathways for riboflavin photoactivation, Type I and Type II. Some of the reactions involved in both the Type I and Type II mechanisms are as follows:

Common reactions:

$$Rf \longrightarrow Rf_1^*, \quad I; \tag{r1}$$

$$Rf_1^* \longrightarrow Rf \quad k1; \tag{r2}$$

$$Rf_1^* \longrightarrow Rf_3^*, \quad k2; \tag{r3}$$

Type I reactions:

$$Rf_3^* + DH \longrightarrow RfH^{\cdot} + D^{\cdot}, \quad k3; \tag{r4}$$

$$2RfH^{\cdot} \longrightarrow Rf + RfH_2, \quad k4; \tag{r5}$$

Type II reactions:

$$Rf_3^* + O_2 \longrightarrow Rf + O_2^1, \quad k5; \tag{r6}$$

$$DH + O_2^1 \longrightarrow D_{ox}, \quad k6; \tag{r7}$$

$$D_{ox} + DH \longrightarrow D-D, \quad k7; \quad CXL \tag{r8}$$

In the reactions described herein, Rf represents riboflavin in the ground state. $Rf_1^*$ represents riboflavin in the excited singlet state. $Rf_3^*$ represents riboflavin in a triplet excited state. $Rf^{\cdot-}$ is the reduced radical anion form of riboflavin. $RfH^{\cdot}$ is the radical form of riboflavin. $RfH_2$ is the reduced form of riboflavin. DH is the substrate. $DH^{\cdot+}$ is the intermediate radical cation. $D^{\cdot}$ is the radical. $D_{ox}$ is the oxidized form of the substrate.

Riboflavin is excited into its triplet excited state $Rf_3^*$ as shown in reactions (r1) to (r3). From the triplet excited state $Rf_3^*$, the riboflavin reacts further, generally according to Type I or Type II mechanisms. In the Type I mechanism, the substrate reacts with the excited state riboflavin to generate radicals or radical ions, respectively, by hydrogen atoms or electron transfer. In Type II mechanism, the excited state riboflavin reacts with oxygen to form singlet molecular oxygen. The singlet molecular oxygen then acts on tissue to produce additional cross-linked bonds.

Oxygen concentration in the cornea is modulated by UVA irradiance and temperature and quickly decreases at the beginning of UVA exposure. Utilizing pulsed light of a specific duty cycle, frequency, and irradiance, input from both Type I and Type II photochemical kinetic mechanisms can be employed to achieve a greater amount of photochemical efficiency. Moreover, utilizing pulsed light allows regulating the rate of reactions involving riboflavin. The rate of reactions may either be increased or decreased, as needed, by regulating, one of the parameters such as the irradiance, the dose, the on/off duty cycle, riboflavin concentration, soak time, and others. Moreover, additional ingredients that affect the reaction and cross-linking rates may be added to the cornea.

If UVA radiation is stopped shortly after oxygen depletion, oxygen concentrations start to increase (replenish). Excess oxygen may be detrimental in the corneal cross-linking process because oxygen is able to inhibit free radical photopolymerization reactions by interacting with radical species to form chain-terminating peroxide molecules. The pulse rate, irradiance, dose, and other parameters can be adjusted to achieve a more optimal oxygen regeneration rate. Calculating and adjusting the oxygen regeneration rate is another example of adjusting the reaction parameters to achieve a desired amount of corneal stiffening.

Oxygen content may be depleted throughout the cornea, by various chemical reactions, except for the very thin corneal layer where oxygen diffusion is able to keep up with the kinetics of the reactions. This diffusion-controlled zone will gradually move deeper into the cornea as the reaction ability of the substrate to uptake oxygen decreases.

Riboflavin is reduced (deactivated) reversibly or irreversibly and/or photo-degraded to a greater extent as irradiance increases. Photon optimization can be achieved by allowing reduced riboflavin to return to ground state riboflavin in Type I reactions. The rate of return of reduced riboflavin to ground state in Type I reactions is determined by a number of factors. These factors include, but are not limited to, on/off duty cycle of pulsed light treatment, pulse rate frequency, irradiance, and dose. Moreover, the riboflavin concentration, soak time, and addition of other agents, including oxidizers, affect the rate of oxygen uptake. These and other parameters, including duty cycle, pulse rate frequency, irradiance, and dose can be selected to achieve more optimal photon efficiency and make efficient use of both Type I as well as Type II photochemical kinetic mechanisms for riboflavin photosensitization. Moreover, these parameters can be selected in such a way as to achieve a more optimal chemical amplification effect.

In addition to the photochemical kinetic reactions (r1)-(r8) above, however, the present inventors have identified the following photochemical kinetic reactions (r9)-(r26) that also occur during riboflavin photoactivation:

$$Rf_3^* \rightarrow Rf, \kappa 8; \tag{r9}$$

$$Rf_3^* + Rf \rightarrow 2RfH^{\prime}, \kappa 9; \tag{r10}$$

$$RfH_2 + O_2 \rightarrow RfH^{\prime} + H^+ + O_2^-, \kappa 10; \tag{r11}$$

$$RfH^{\prime} + O_2 \rightarrow Rf + H^+ + O_2^-, \kappa 11; \tag{r12}$$

$$2RfH_2 + O_2^- \rightarrow 2RfH^{\prime} + H_2O_2, \kappa 12; \tag{r13}$$

$$2RfH^{\prime} + O_2^- \rightarrow 2Rf + H_2O_2, \kappa 13; \tag{r14}$$

$$RfH^{\prime} + H_2O_2 \rightarrow OH^{\prime} + Rf + H_2O, \kappa 14; \tag{r15}$$

$$OH^{\prime} + DH \rightarrow D^{\prime} + H_2O, \kappa 15; \tag{r16}$$

$$D^{\prime} + D^{\prime} \rightarrow D-D, \kappa 16; \; CXL \tag{r17}$$

$$O_2^1 \rightarrow O_2, \kappa 18; \tag{r18}$$

$$D^{\prime} + RfH_2 \rightarrow RfH^{\prime} + DH, \kappa 19; \tag{r19}$$

$$Rf + Rf \underset{\kappa_a^-}{\overset{\kappa_a^+}{\rightleftharpoons}} A_1, \kappa_a = \kappa_a^+ / \kappa_a^- \tag{r20}$$

$$RfH_2 + RfH_2 \underset{\kappa_a^-}{\overset{\kappa_a^+}{\rightleftharpoons}} A_2, \kappa_a = \kappa_a^+ / \kappa_a^- \tag{r21}$$

$$Rf + RfH_2 \underset{\kappa_b^-}{\overset{\kappa_b^+}{\rightleftharpoons}} A_3, \kappa_b = \kappa_b^+ / \kappa_b^- \tag{r22}$$

-continued $$Rf_1^* + A \rightarrow Rf + A, \kappa_{1a} \quad (r23)$$

$$Rf_3^* + A \rightarrow Rf + A, \kappa_{3a} \quad (r24)$$

$$2O_2^- \rightarrow O_2 + H_2O_2, \kappa_{12} \quad (r25)$$

$$OH^\circ + CXL \rightarrow \text{inert products}, \kappa_{OH} \quad (r26)$$

Figure 2A:
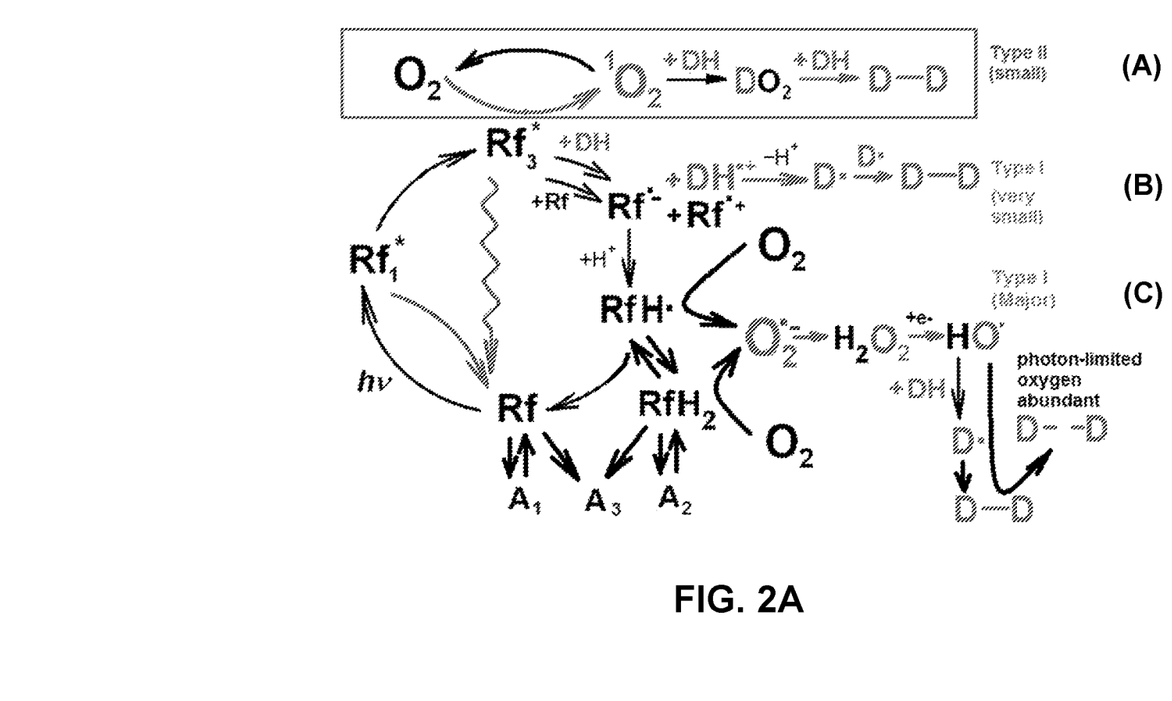
FIG. 2A illustrates a diagram for photochemical kinetic reactions involving riboflavin and photoactivating light (e.g., ultraviolet A (UVA) light) applied during a corneal cross-linking treatment, according to aspects of the present disclosure.

FIG. 2A illustrates a diagram for the photochemical kinetic reactions provided in reactions (r1) through (r26) above. The diagram summarizes photochemical transformations of riboflavin (Rf) under UVA photoactivating light and its interactions with various donors (DH) via electron transfer. As shown, cross-linking activity occurs: (A) through the presence of singlet oxygen in reactions (r6) through (r8) (Type II mechanism); (B) without using oxygen in reactions (r4) and (r17) (Type I mechanism); and (C) through the presence of peroxide ($H_2O_2$), superoxide ($O_2^-$), and hydroxyl radicals ($\cdot OH$) in reactions (r13) through (r17).

As shown in FIG. 2A, the present inventors have also determined that the cross-linking activity is generated to a greater degree from reactions involving peroxide, superoxide, and hydroxyl radicals. Cross-linking activity is generated to a lesser degree from reactions involving singlet oxygen and from non-oxygen reactions. Some models based on the reactions (r1)-(r26) can account for the level of cross-linking activity generated by the respective reactions. For instance, where singlet oxygen plays a smaller role in generating cross-linking activity, models may be simplified by treating the cross-linking activity resulting from singlet oxygen as a constant.

All the reactions start from $Rf_3^*$ as provided in reactions (r1)-(r3). The quenching of $Rf_3^*$ occurs through chemical reaction with ground state Rf in reaction (r10), and through deactivation by the interaction with water in reaction (r9).

As described above, excess oxygen may be detrimental in corneal cross-linking process. As shown in FIG. 2A, when the system becomes photon-limited and oxygen-abundant, cross-links can be broken from further reactions involving superoxide, peroxide, and hydroxyl radicals. Indeed, in some cases, excess oxygen may result in net destruction of cross-links versus generation of cross-links.

As described above, a large variety of factors affect the rate of the cross-linking reaction and the amount of biomechanical stiffness achieved due to cross-linking. A number of these factors are interrelated, such that changing one factor may have an unexpected effect on another factor. However, a more comprehensive model for understanding the relationship between different factors for cross-linking treatment is provided by the photochemical kinetic reactions (r1)-(r26) identified above. Accordingly, systems and methods can adjust various parameters for cross-linking treatment according to this photochemical kinetic cross-linking model, which provides a unified description of oxygen dynamics and cross-linking activity. The model can be employed to evaluate expected outcomes based on different combinations of treatment parameters and to identify the combination of treatment parameters that provides the desired result. The parameters, for example, may include, but are not limited to: the concentration(s) and/or soak times of the applied cross-linking agent; the dose(s), wavelength(s), irradiance(s), duration(s), and/or on/off duty cycle(s) of the photoactivating light; the oxygenation conditions in the tissue; and/or presence of additional agents and solutions.

Figure 2B:
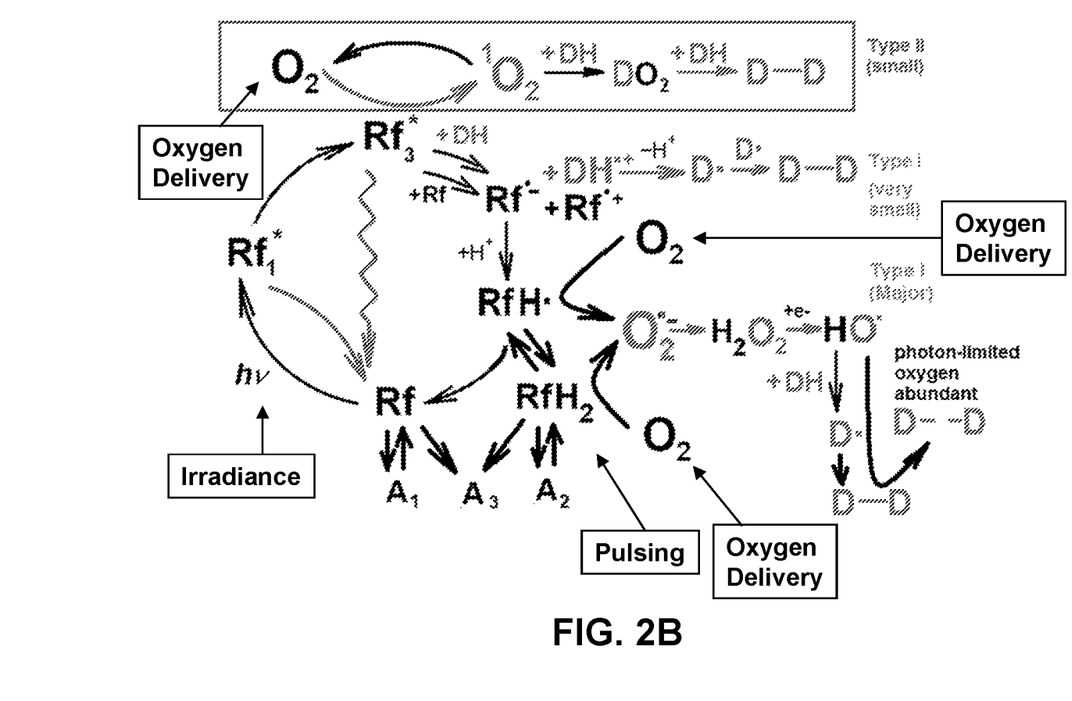
FIG. 2B illustrates a diagram for parameters that can affect the photochemical kinetic reactions shown in FIG. 2A.

As shown in FIG. 2B, aspects of the system of reactions can be affected by different parameters. For instance, the irradiance at which photoactivating light is delivered to the system affects the photons available in the system to generate $Rf_3^*$ for subsequent reactions. Additionally, delivering greater oxygen into the system drives the oxygen-based reactions. Meanwhile, pulsing the photoactivating light affects the ability of the reduced riboflavin to return to ground state riboflavin by allowing additional time for oxygen diffusion. Of course, other parameters can be varied to control the system of reactions.

Further aspects of the photochemical kinetic reactions provided in reactions (r1)-(r26) are described in U.S. Patent Application Publication No. 2016/0310319, filed Apr. 27, 2016 and titled "Systems and Methods for Cross-Linking Treatments of an Eye," the contents of which are incorporated entirely herein by reference.

When light of a particular wavelength is applied to a cross-linking agent, such as riboflavin, the light can excite the cross-linking agent and cause the cross-linking agent to fluoresce. As such, an excitation light can be employed to cause a cross-linking agent in corneal tissue to fluoresce and determine how the cross-linking agent is distributed in the corneal tissue. When an image of the cornea is taken during the application of the excitation light, the intensity (magnitude) of the fluorescence, for instance, can be measured to determine the amount, i.e., dose, of cross-linking agent taken up by the corneal tissue. Using these principles, dosimetry systems can determine the presence and distribution of the cross-linking agent in the cornea by capturing one or more images of the fluorescence from the cross-linking agent as it responds to the excitation light. Aspects of such systems are described, for instance, in U.S. Pat. No. 9,020,580, issued Apr. 28, 2015 and titled "Systems and Methods for Monitoring Time Based Photo Active Agent Delivery or Photo Active Marker Presence," and U.S. Patent Application Publication No. 2016/0338588, filed May 23, 2016 and titled "Systems and Methods for Monitoring Cross-Linking Activity for Corneal Treatments," the contents of these applications being incorporating entirely herein by reference. In particular, U.S. Pat. No. 9,020,580 discloses an example dosimetry system that employs a modified Scheimpflug configuration. Meanwhile, U.S. Patent Application Publication No. 2016/0338588 discloses the use of hyperspectral imaging to analyze fluorescence.

In general, the structure of the cornea includes five layers. From the outer surface of the eye inward, these are: (1) epithelium, (2) Bowman's layer, (3) stroma, (4) Descemet's membrane, and (5) endothelium. During example cross-linking treatments, the stroma is treated with riboflavin, a photosensitizer, and ultraviolet (UV) light is delivered to the cornea to activate the riboflavin in the stroma. Upon absorbing UV radiation, riboflavin undergoes a reaction with oxygen in which reactive oxygen species and other radicals are produced. These reactive oxygen species and other radicals further interact with the collagen fibrils to induce covalent bonds that bind together amino acids of the collagen fibrils, thereby cross-linking the fibrils. The photo-oxidative induction of collagen cross-linking enhances the biomechanical strength of the stroma, and can provide therapeutic benefits for certain ophthalmic conditions, such as keratoconus, or generate refractive changes to correct myopia, hyperopia and/or astigmatism.

As the outermost barrier of the cornea, the epithelium protects the cornea from bacteria and the free flow of fluids into the stroma. The epithelium is formed from several layers of cells. The innermost layer is the basal epithelial layer, which includes a single layer of columnar basal cells that adheres to Bowman's layer of the stroma. The basal epithelial layer is then followed by two to three superbasal epithelial layers, which includes wing cells that are polyhedral in shape. The superbasal epithelial layers are followed by two to three apical layers of superficial squamous cells with flat nuclei. The superbasal squamous layers are covered by a tear film, which is a lipid, aqueous, and mucous film. The tight junctions formed by edge-to-edge contact by the superficial squamous cells allow the epithelium to act as an effective barrier.

The layers of the epithelium are constantly undergoing mitosis. The life cycle of these epithelial cells starts with the basal cells maturing to wing cells, which mature to squamous cells, which then age and slough off into the tear film.

The epithelium functions to regulate nutrients, including oxygen, that are admitted into the stromal tissue from the tear film. This regulation is carried out via the epithelium's physiological "pumps" that are driven by osmotic pressure across the epithelium due to differential concentrations of barrier-permeable solutes on either side of the epithelium. When healthy, certain nutrients in the tear film that become depleted within the stroma can permeate the epithelium via osmotic pressure to resupply the stroma. However, while oxygen and some other small molecule nutrients can reach the stroma according to this mechanism, certain photosensitizers cannot pass through the epithelium.

Riboflavin, for example, is a relatively large, hydrophilic molecule that cannot penetrate the tight junctions of the epithelium. The epithelium slows the amount of riboflavin that can penetrate the stroma. Thus, a variety of approaches have been employed to overcome low riboflavin diffusivity and deliver sufficient concentrations of riboflavin to the stroma for performing corneal cross-linking treatments. According to one approach, the epithelium is removed (epithelium debridement) before a riboflavin solution is applied directly to the stroma. Although removing the epithelium allows riboflavin to reach the stroma, the approach is associated with patient discomfort, risks of infection, and other possible complications.

Meanwhile, other approaches avoid epithelial debridement. For example, riboflavin may be provided in a formulation that allows the cross-linking agent to pass through the epithelium. Such formulations are described, for example, in U.S Patent Application Publication No. 2010/0286156, filed on May 6, 2009 and titled "Collyrium for the Treatment of Conical Cornea with Cross-Linking Trans-Epithelial Technique, and in U.S. Patent Application Publication No. 2013/0267528, filed on Jan. 4, 2013 and titled "Trans-Epithelial Osmotic Collyrium for the Treatment of Keratoconus," the contents of these applications being incorporated entirely herein by reference. In particular, some riboflavin formulations include ionic agents, such as benzalkonium chloride (BAC), with a specific osmolarity of sodium chloride (NaCl). Although such formulations may enhance permeability of the epithelium, they are disadvantageously corrosive to the epithelium, beyond the tight junctions.

Another class of riboflavin formulations enhances the permeability of the epithelium sufficiently to allow relatively large hydrophilic riboflavin molecules (or Flavin mononucleotide (FMN), or riboflavin-5'-phosphate, molecules) to pass through the epithelium without debridement, but the permeability is not enhanced to a point where the epithelium becomes damaged. To enhance permeability, such formulations employ a non-ionic agent that is chosen using the Hydrophile-Lipophile Balance (HLB) system. Aspects of such permeability enhancers are described, for instance, in U.S. Patent Application Publication No. 2017/0021021, filed Jul. 21, 2016 and titled "Systems and Methods for Treatments of an Eye with a Photosensitizer," the contents of which are incorporated entirely herein by reference.

The HLB of a permeability enhancer indicates the balance of hydrophilic and lipophilic groups in the molecular structure of the enhancer. Permeability enhancers (or emulsifiers) for the epithelium include a molecule which has both hydrophilic and lipophilic groups. Molecules with HLB number below 9 are considered lipophilic and those above 11 as hydrophilic. Molecules with HLB number between 9 and 11 are intermediate.

For the corneal epithelium, a HLB number that is too great or too small does not help the passage of a photosensitizer through the epithelium. A specific HLB range enhances movement of a photosensitizer through the epithelium. Thus, aspects of the present disclosure employ non-ionic agents that have a hydrophilic/lipophilic balance to achieve optimized diffusivity through the epithelium and the stroma. Advantageously, non-ionic agents are also less corrosive and damaging to the epithelium than ionic agents, such as BAC.

For riboflavin, the HLB range for more effective permeability enhancers has been experimentally determined by the inventors to be between approximately 12.6 and approximately 14.6. A class of permeability enhancers includes various forms of polyethylene glycol (PEG) with different aliphatic chain lengths. According to example embodiments, some riboflavin formulations include specific concentrations of Polidocanol (Polyoxyethylene (9) lauryl ether), which has a HLB number of approximately 13.6.

To calculate the HLB for molecules or combinations of molecules where the hydrophilic portion consists of ethylene oxide only, the formula is:

$$HLB = E/5, \text{ where } E = \text{weight percentage oxyethylene content.}$$

In general, the HLB range for enhancers that achieve more effective permeability may vary according to different aspects of the formulation. In particular, the HLB range for more optimal enhancers may vary according to the photosensitizer employed in the formulation. For instance, more optimal permeability might be achieved for other photosensitizers, such as Rose Bengal, by employing enhancers in a HLB range that is different from that for riboflavin (e.g., HLB of approximately 12.6 to approximately 14.6).

Furthermore, the formulation may include other additives that may affect the HLB range for more optimal enhancers. For instance, riboflavin formulations may also include iron ions, such as Fe(II). Additives that may be included in photosensitizer formulations are described, for example, in U.S. Patent Application Publication No. 2014/0343480, filed May 19, 2014 and titled "Systems, Methods, and Compositions for Cross-linking," and U.S. Patent Publication Application No. 2016/0175442, filed Dec. 2, 2015and titled "Systems, Methods, and Compositions for Cross-linking," the contents of these applications being incorporated entirely herein by reference. Other additives, for instance, include copper, manganese, chromium, vanadium, aluminum, cobalt, mercury, cadmium, nickel, arsenic, 2,3-butanedione, and folic acid.

Additionally, several permeability enhancers may be combined to achieve a specific HLB that achieves more effective permeability for the epithelium. Two or more enhancers may be combined to achieve a very specific HLB number, where a single enhancer may provide less optimal permeability. Additionally, combining different enhancers might offer other desirable properties of the final formulation with regard to solubility, viscosity, stability or some other desirable attribute.

Additionally or alternatively, another solution and/or mechanical forces may be applied to enhance the permeability of the epithelium and allow the riboflavin to pass more easily through the epithelium. Examples of approaches for enhancing or otherwise controlling the delivery of a cross-linking agent to the underlying regions of the cornea are described, for example, in U.S. Patent Application Publication No. 2011/0288466, filed Apr. 13, 2011 and titled "Systems and Methods for Activating Cross-Linking in an Eye," and U.S. Patent Application Publication No. 2012/0289886, filed May 18, 2012 and titled "Controlled Application of Cross-Linking Agent," the contents of these applications being incorporated entirely herein by reference.

Systems and methods may enhance the permeability of the epithelium by disrupting (e.g., removing) only the two to three apical layers of superficial squamous cells, which form the tight junctions for the barrier function of the epithelium. Such disruption allows para-cellular drug delivery to proceed unhindered. With this approach rapid uptake of photosensitizer (e.g., cross-linking agent) formulations in the stroma can be achieved without using corrosive additives, such as BAC. This effective drug delivery allows acute focal treatment of ocular disease or refractive disorders with the photosensitizer formulations.

As described above, a large variety of factors affect the rate of the cross-linking reaction and the amount of biomechanical stiffness achieved due to cross-linking. Indeed, enhancing permeability through the disruption of the apical layers to deliver high concentrations of cross-linking agent to the stroma is only one aspect of achieving efficient cross-linking. Thus, such permeability enhancement may also be combined with the use of specific cross-linking agent formulations as well as oxygen. Aspects of systems and methods that enhance the permeability of the epithelium by disrupting apical layers of superficial squamous cells are described, for instance, in International Patent Publication No. WO 2018/031529, filed Dec. 12, 2016 and titled "Systems and Methods for Cross-Linking Treatments of an Eye," the contents of which are incorporated entirely herein by reference. In some cases, the apical layers are mechanically disrupted. In other cases, the apical layers are removed by an excimer laser.

According to aspects of the present disclosure, systems and methods may employ different phases for applying formulations for treating an eye, e.g., cross-linking treatments. For instance, in some epithelium-on cross-linking treatments, formulations are applied according to different phases to enhance penetration through the epithelium and promote desired delivery of photosensitizer, e.g., riboflavin, formulations into the cornea. In other treatments, different phases may be employed to deliver antibiotics, biologics, etc., in a series of specific drug formulations.

A drug delivery system, e.g., a kit, may provide different solutions that are applied for one or more respective phases of a treatment. Such phases may include preparatory surface conditioning, therapeutic agent delivery, therapeutic action enhancement, and/or post-treatment. Each of these phases may involve one or more different solutions, e.g., drug formulations. Furthermore, each of the phases may involve the use of devices, e.g., sponges, epithelium disruption devices, and/or other specialized surface modification devices. It is contemplated that two or more phases may be combined and a single solution can be applied to achieve the desired outcome(s) of each phase.

Aspects of a multi-phase approach may involve features described in U.S. Patent Application Publication No. 2017/0296383, U.S. Patent Application Publication No. 2017/0021021, and International Patent Publication No. WO 2018/031529 as described herein. Further aspects of the multi-phase approach may also involve features described in U.S. Patent Application Publication No. 2016/0175442, filed Dec. 2, 2015 and titled "Systems, Methods, and Compositions for Cross-Linking," U.S. Patent Application Publication No. 2017/0156926, filed Dec. 5, 2016 and titled "Systems and Methods for Treating an Eye," the contents of these applications being incorporated entirely herein by reference.

Figure 3:
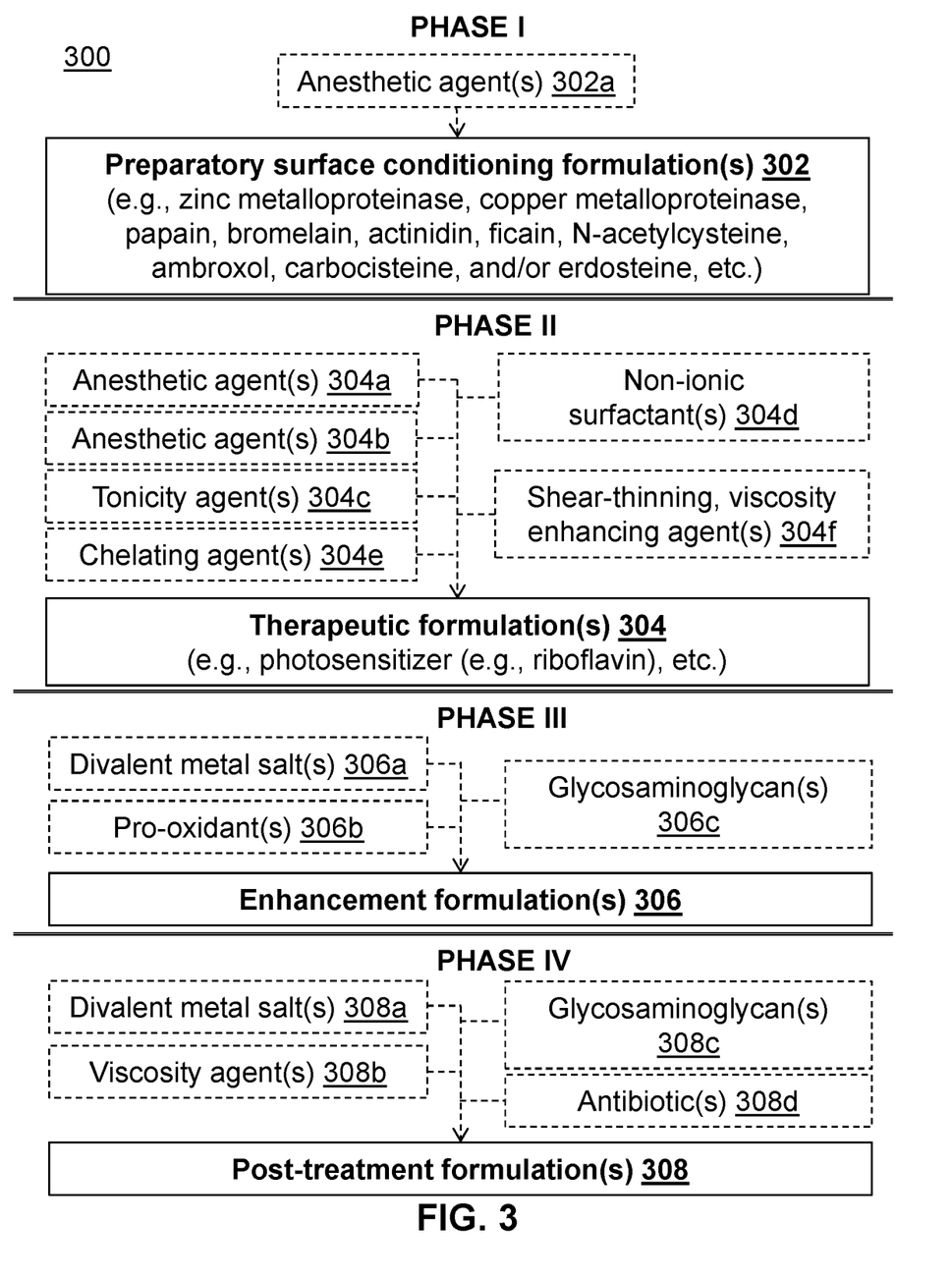
FIG. 3 illustrates an example approach for applying formulations in phases to treat an eye, according to aspects of the present disclosure.

As FIG. 3 illustrates, an example treatment 300 may include at least four phases I-IV to provide an enhanced treatment for epithelium-on corneal cross-linking treatment.

Phase I: Preparatory Surface Conditioning

In Phase I, one or more formulations 302 are applied to prepare the cornea for further delivery of one or more therapeutic agents. Mucin in the glycocolyx layer is the foremost anterior component in creating a barrier for the cornea and restricting epithelial permeability. The membrane-associated mucin MUC16, a heavily O-glycosylated transmembrane protein, is expressed by the ocular surface epithelia and localized on the tips of the surface microplicae. It is thought that MUC16 provides a disadhesive barrier to the epithelial membrane. Two other membrane-associated mucins expressed by ocular surface epithelia, MUC1 and MUC4, are multifunctional and have signaling capabilities through their cytoplasmic tails and EGF-like domains, respectively. Because the MUC16 cytoplasmic tail contains a polybasic amino acid sequence, it may interact with the actin cytoskeleton through ezrin/radixin/moesin (ERM) actin-binding proteins.

In view of the barrier created by mucin, the one or more preparatory surface conditioning formulations 302 in Phase I may remove or liquefy mucin from the apical microvilli on the epithelial surface. The agents in such formulations 302 are tailored to break or disrupt MUC16, MUC1, and MUC4, along their binding sites and may include enzymes such as zinc or copper metalloproteinases (not to be used in combination with chelating agents, such as ethylenediaminetetraacetic acid (EDTA), as they may be inactivated) or other agents such as papain, bromelain, actinidin, ficain, N-acetylcysteine, ambroxol, carbocisteine, and erdosteine. The formulations 302 may be designed for optimal mucin removal, minimizing application time as well as epithelial damage.

The one or more preparatory surface conditioning formulations 302 may also include anesthetic properties. In example implementations, the eye receives one or more drops which may include one or more anesthetic agents 302a containing a mucin removing/liquifying formulation. In some cases, the drops may be applied in a single instillation. In other cases, the drops may be applied multiple times over the course of several minutes. The anesthetic agent 302a applied to the surface of the eye may affect the permeability of the epithelial layer via a different mechanism of action than other permeability enhancers. The drops may include a topical formulation containing pilocarpine, but may also be a formulation of proparacaine, tetracaine, oxybuprocaine, or any combination thereof.

In some embodiments, the preparatory surface conditioning formulation(s) facilitate removal through mechanical techniques. Such mechanical techniques may employ a sponge to wipe the cornea and remove the residual mucin layer from the surface. The physical removal of the mucin layer may also remove some of the epithelial cells that are attached to the mucin. The removal of the mucin and the attached epithelial cells increases the permeability of the eye. The formulations 302 may be configured to liquefy and thin the mucin layer in a manner that minimizes the applied pressure, number of wipes, and/or amount of rinsing. Aspects of wiping the surface, e.g., applied pressure, may be controlled by mechanisms disclosed in International Patent Publication No. WO 2018/031529 as described above. Additionally or alternatively, the eye may be irrigated, e.g., with multiple drops, to rinse away the mucin.

Phase II: Therapeutic Agent Delivery

In Phase II, one or more therapeutic formulations 304 are applied to deliver one or more therapeutic agents to the cornea. The one or more therapeutic agents may include a photosensitizer, such as riboflavin, for cross-linking treatments as described above. The tight junctions of the cornea also create a barrier and restrict epithelial permeability. The one or more therapeutic formulations 304 may enhance drug delivery through the corneal epithelium into the corneal stroma. In particular, such therapeutic formulations 304 may provide optimized delivery of the one or more therapeutic agents through the tight junctions, the apical superficial cells, wing cells and basal cells of the epithelium. Such therapeutic formulations 304 may also be configured to minimize application time as well as cell damage.

In addition to the permeability enhancement provided in Phase I, the one or more therapeutic formulations 304 used during Phase II may include other agents, such as BAC or EDTA as described above, to further enhance permeability of the epithelial layer. One or more of the following approaches and/or formulation characteristics have been found to provide enhanced penetration and promote delivery of the one or more therapeutic agents:

- Multiple drops of the therapeutic formulation(s) 304 are applied to the eye for a prolonged treatment period.
- The therapeutic formulation(s) 304 has (have) higher viscosity for enhanced drug delivery (depending on specific ranges of osmolality, e.g., if viscosity is increased by a high concentration of dextran, osmotic flow of fluid may occur out of the cornea, against the direction of desired drug delivery).
- The therapeutic formulation(s) 304 contain(s) one or more ionic agents, such BAC, for enhanced penetration and drug delivery, but are applied with lower concentration or shorter exposure times due to possible damage to the epithelial layer.
- The therapeutic formulation(s) 304 contain(s) one or more non-ionic agents, such as PEG-40 or Tyloxapol, to achieve a specified hydrophilic/lipophilic balance (HLB) and enhanced penetration and drug delivery.
- The therapeutic formulation(s) 304 contain(s) one or more chelating agents, such as EDTA, to open the tight junctions in the corneal tissue.
- The therapeutic formulation(s) 304 contain(s) one or more co-solvents as tonicity agents.
- The therapeutic formulation(s) 304 contain(s) one or more osmotic agents to control corneal thickness.
- Sub-therapeutic and non-active analgesic(s) are applied for enhanced penetration and drug delivery.
- Higher concentrations of the active agent are applied to drive drug delivery, but depend on time dependence with regard to concentration as the higher concentrations may result in less optimal cross-linking in the cornea due to high levels of UV absorption and the formation of aggregates (dimers) in the tissues.

During Phase II, the one or more therapeutic formulations 304 can (1) provide effective therapeutic agent delivery through the epithelium and into the stroma, (2) control the thickness of the cornea (i.e., avoid excessive corneal thinning), and/or (3) minimize toxicity to the epithelial layer that may damage the epithelium. The one or more therapeutic formulations 304 may be iso-osmotic using tonicity agents that are sufficiently low in molecular weight (MW) so that they can penetrate the cornea to avoid thinning the cornea.

Anesthetic/Analgesic Agents

The one or more therapeutic formulations 304 may include one or more active anesthetic agents 304a and/or one or more analgesic agents 304b that can provide additional penetration enhancement. Anesthetic or analgesic agents not considered to be pharmaceutically active agents in the formulation may be present as penetration-enhancing agents. This is achieved by either using a sub-therapeutic level of active anesthetic agent or using another analgesic agent that is not considered as an ophthalmic active agent. For instance, menthol is an analgesic agent that can have a beneficial effect on ophthalmic drug delivery, but is not considered to be an active agent for ophthalmic use. There are several ingredients that are structurally similar to menthol and provide various levels of analgesia. These are listed in TABLE 1 below as options that may implemented. The solubility of menthol in water is relatively low (0.04%); it may be added to a formulation by dissolving it in propylene glycol prior to addition to the formulation.

TABLE 1

Anesthetic/analgesic agents for penetration enhancement

| Type/Mechanism of Penetration Enhancement | Agents |
| --- | --- |
| Sub-therapeutic level of anesthetic as penetration enhancer | pilocarpine<br>tetracaine<br>oxybuprocaine<br>proparacaine |
| Non-active analgesic as penetration enhancer | menthol<br>benzyl alcohol<br>phenylethyl alcohol |

Co-Solvents as Tonicity Agents

Other penetration-enhancing agents may include a non-ionic co-solvent as a tonicity agent in a formulation. Tonicity agents that are sufficiently low in MW can readily diffuse into the tissues. The therapeutic agent having good solubility in the co-solvent can experience enhanced delivery through the epithelium and into the stroma. Propylene glycol may be a penetration enhancer for topical formulations by this mechanism of action. Thus, the one or more therapeutic formulations 304 may include one or more co-solvents as tonicity agents 304c. A list of co-solvents that may be used to increase therapeutic agent delivery via this mechanism of action and suitable for ophthalmic use are shown in TABLE 2.

TABLE 2

Co-solvents, suitable for ophthalmic use, for penetration enhancement

| Co-solvent | MW | USP/NF | IIGDB % (Ophthalmic) | Solubility of FMN |
|---|---|---|---|---|
| glycerin | 92 | USP | 10 | 8.9 mg/mL |
| propylene glycol | 76 | USP | 5 | 5.7 mg/mL |
| PEG-8 | 400 | NF | 5 | — |
| ethanol | 46 | USP | 1.4 | 0.08 mg/mL |
| benzyl alcohol | 108 | NF | NA | — [A] |
| phenylethyl alcohol | 122 | NF | 0.5 | — |
| triacetin | 218 | NF | — | — |

[A] The partition coefficient between benzyl alcohol and water was 0.01 for FMN.

Both propylene glycol and glycerin may be employed as ingredients in dry eye drops. Glycerin has been evaluated for therapeutic agent delivery into the eye and is capable of penetrating the cornea. For instance, FMN has solubility in propylene glycol and glycerin that is greater than the total concentration in the formulation. As the co-solvent penetrates the tissues, it may carry some FMN into the tissues as well enhancing the delivery. Replacing the sodium chloride with glycerin or propylene glycol should not negatively impact therapeutic agent delivery of the FMN.

Non-Ionic Surfactants

The one or more therapeutic formulations 304 may include one or more non-ionic surfactants 304d. As described above, ionic surfactants, such as BAC, enhance penetration but may be toxic to the epithelium. Non-ionic surfactants provide penetration enhancement but with less toxicity to the epithelium. Non-ionic surfactants are higher in MW than cationic surfactants. Penetration enhancement by non-ionic surfactants is correlated with the HLB of the surfactant. For instance, some riboflavin formulations include non-ionic surfactant(s) with a target HLB number of approximately 13.6.

TABLE 3 shows a listing of non-ionic surfactants. The list of surfactants in this table is restricted to those with higher MW than BAC, because it is postulated that surfactants unable to penetrate the tissues may also exhibit lower toxicity to the tissues (BAC has a MW of 360 and HLB>24).

TABLE 3

Surfactants, suitable for ophthalmic use, with HLB values of about 13-15 and MW significantly greater than BAC

| Surfactant | HLB | USP/NF | MW | IIGDB % (Ophthalmic) |
|---|---|---|---|---|
| poloxamer 407 | 18-23 | NF | 12500 | 0.2 |
| tetronic 1107 | 18-23 | — | 15000 | — |
| tetronic 1304 | 12-18 | — | 10500 | — |
| polysorbate 80 | 15 | NF | 1310 | 1 |
| PEG-40 hydrogenated castor oil | 15 | NF | 2719 | 0.5 |
| lecithin | 15 | NF | 644 | — |
| polysorbate 60 | 14.9 | NF | 1312 | 1 |
| PEG-35 castor oil | 13 | NF | 2493 | 5 |
| tocophersolan (TPGS) | 13 | NF | 1513 | 0.5 |
| nonoxynol-9 | 13 | NF | 616 | 0.13 |
| tyloxapol | 12.9 | USP | 4900 | 0.3 |

EDTA Versus Citrate as Chelating Agent

The one or more therapeutic formulations 304 may include one or more chelating agents 304e. EDTA is a chelating agent and acts as a penetration enhancer by binding to calcium and opening tight junctions in the epithelium. In addition, EDTA may provide an antioxidant function in the formulation. In cross-linking activities, however, too much EDTA can cause quenching of photochemical kinetic reactions and thus should be added in specific concentrations. To reduce the toxicity of a formulation while still providing penetration enhancement, the EDTA may be replaced with citrate (e.g., sodium citrate). Citrate is also able to bind calcium albeit not as effectively as EDTA. Combinations of EDTA and citrate allow for optimum calcium chelation while keeping the concentration of EDTA at concentrations that do not affect cross-linking efficiency.

Shear-Thinning Viscosity Enhancing Agents

The one or more therapeutic formulations 304 may include one or more shear-thinning, viscosity enhancing agents 304f. Viscosity-increasing agents are used to improve the retention time of the formulation on the surface of the eye to increase drug delivery. Agents, such as dextran and hydroxypropyl methylcellulose (HPMC), provide Newtonian or pseudo-Newtonian viscosity enhancement. Meanwhile, carbomer, carboxymethyl cellulose, xanthan gum, and hyaluronic acid are polymers that provide viscosity-enhancement and exhibit significant shear-thinning behavior. The advantage of shear-thinning polymers is that the viscosity at low shear (at rest, between eye blinks, etc.) can be increased to over 100 000 cP while keeping the high shear viscosity (when squeezed from the dropper bottle, during eye blinks) at levels of less than 200 cP so that it can flow as a liquid and not cause discomfort on the eye. Using this type of formulation additive, for instance, may allow application of the drug without the use of a speculum and allow the patient to sit up during Phases I and II. The act of blinking in Phase I formulations may have enough shear force to gently remove the mucin layer. Additives in Phase II formulations may have ingredients that help rinse the viscosity agents of Phase I formulations off the surface of the eye.

TABLE 4

Shear-thinning, viscosity-increasing agents suitable for ophthalmic use to increase drug delivery of active agents

| Shear-thinning, Viscosity-increasing Agent | USP/NF | IIGDB % (Ophthalmic) |
|---|---|---|
| carbomer 980 CARBOMER HOMOPOLYMER TYPE C | NF | 4 |
| polycarbophil | USP | 0.9 |
| gellan gum | NF | 0.6 |
| xanthan gum | NF | 0.6 |
| carboxymethyl cellulose sodium | NF | 0.5 |
| sodium hyaluronate | — (EP) | — |

One example of a shear-thinning agent listed in TABLE 4 is carbomer. Carbomer is a polymer that has a useful property: the viscosity-increasing property is highly salt sensitive. When salt is added to carbomer-thickened solutions, the polymer dehydrates and loses its viscosity. This property maybe utilized to allow this polymer to be more easily rinsed from the eye with the addition of a secondary Phase I salt formulation or a first Phase II formulation.

The level of carbomer may be 0.3%. At this level, the high shear viscosity is approximately 100 cP to 300 cP and the formulation still flows as a liquid under high shear. The viscosity at low shear is approximately 10,000 cP to 100,000 cP which significantly slows drainage from the surface. A higher level of carbomer may result in a thickness that does not permit the formulation to be easily spread on the surface of the eye. Carbomer may drop the pH of the formulation down to about 3 and may require neutralization with the addition of tromethamine. The amount of tromethamine can be added to bring the pH to approximately 7.2. This level of tromethamine is within the level allowed as an inactive ingredient.

EDTA may be reduced in formulations including carbomer, but not removed completely. The carbomer polymer is very sensitive to salts and a low level of EDTA may be used to protect the viscosity of the carbomer from salt contaminants (e.g., calcium, magnesium, etc.). The buffer is simplified by removing the monobasic salt. The inclusion of some phosphate buffer provides some buffer capacity at the pH of the formulation but the level is minimized, again, due to the salt sensitivity of the carbomer polymer.

When using a thickening agent, such as those listed in TABLE 4, high MW polymers are too large to pass through a sterile filtration membrane and necessitate appropriate manufacturing processes. For instance, a split-phase manufacturing process may be employed, where an autoclaved vehicle containing sterilized carbomer is combined with a sterile-filtered solution to prepare the final product.

Physical Retention of Solution on Surface of Eye

Another option for enhancing the retention of the drug on the surface of the eye during Phase II involves a controlled-release drug delivery approach. For instance, an ocular insert may be employed to dissolve slowly over approximately 20 minutes to 30 minutes. The insert may include a polymer matrix (e.g., povidone or HPMC), one of the shear-thinning agents shown above, and a suitable amount of the active ingredient.

Alternatively, a drug delivery device as described in U.S. Patent Application Publication No. 2017/0296383 may be employed. The ability to retain the drug on the surface of the eye allows the solutions of Phase I and Phase II to be delivered while the patient is seated upright, without requiring a technician to administer drops repeatedly during the time period.

Phase III: Therapeutic Action Enhancement

In Phase III, one or more enhancement formulations 306 may be applied to clear the epithelium of the one or more therapeutic agents 304 without diluting the one or more therapeutic agents 304 delivered to the stroma. The one or more enhancement formulations 306 can minimize toxicity to the epithelium by removing any residual therapeutic agent that may either absorb and/or create reactive oxygen species that can damage epithelial cells. The one or more enhancement formulations 306 may also minimize treatment time. For cross-linking treatments, removal of residual therapeutic agent in the epithelium also enhances cross-linking efficiency of the stroma by reducing photon absorption and promoting more efficient oxygen diffusion through the epithelium. During cross-linking treatments, the one or more enhancement formulations 306 may be applied prior to and/or during the application of photoactivating light, e.g., UVA light.

Additionally, the one or more enhancement formulations 306 may also close the tight junctions and maintain specific hydration properties of the cornea. Maintenance of hydration stabilizes the thickness of the cornea permits more repeatable and predictable control of cross-linking activity.

Phase III may also include the addition of pro-oxidants in the stroma that enhance the cross-linking activity as described above. Additionally or alternatively, Phase III may include controlling temperature of the one or more solutions during application. For example, increasing temperature of the one or more photosensitizer formulations may increase the photochemical kinetic reaction rate associated with cross-linking activity.

The one or more enhancement formulations 306 in Phase III may include one or more of the following characteristics:
 The enhancement formulation(s) 306 do not include antioxidants (e.g., no EDTA, no tocophersolan, no glutathione) that might inhibit the cross-linking reactions initiated by riboflavin.
 The enhancement formulation(s) 306 do not contain other components that inhibit cross-linking performance (e.g., no tromethamine, no other amines, no UV-absorbing compounds).
 The enhancement formulation(s) 306 contain(s) one or more divalent metal salts 306a to replace those removed from the tight junctions by chelants (e.g., magnesium salts, calcium salts).
 The enhancement formulation(s) 306 contain(s) one or more pro-oxidants 306b that enhance cross-linking reactions by promoting oxidation (e.g., iron salts, zinc salts, peroxide donating ingredients, etc.)
 The enhancement formulation(s) 306 contain(s) a low MW co-solvent designed to penetrate into the cornea, and carry with it, the riboflavin active that may be present on the surface or in the corneal epithelium.
 The enhancement formulation(s) 306 may contain one or more glycosaminoglycans 306c, e.g., a nonsulfated glycosaminoglycan such as a hyaluronic acid.

Phase IV: Final Post-Treatment

In Phase IV, one or more post-treatment formulations 308 are applied to rinse, from the epithelial layer, any residual formulation(s) and by-product(s) from other steps in the eye treatment. For instance, in a cross-linking treatment, the one or more post-treatment formulations 308 may be applied upon the application of photoactivating light, e.g., after Phase III. The one or more post-treatment formulations 308 may enhance reconditioning of the corneal tissue, promote healing processes, and/or prevent infection. The one or more post-treatment formulations 308 may include specific antibiotics, special bandages, lubricants, etc. Phase IV may also include controlling temperature, viscosity, and/or other aspects of the one or more solutions.

The one or more post-treatment formulations 308 in Phase IV may include one or more of the following characteristics:
 The post-treatment formulation(s) 308 contain(s) one or more divalent metal salts 308a to replace those removed from the tight junctions by chelants (e.g., magnesium salts, calcium salts).
 The post-treatment formulation(s) 308 may contain one or more special viscosity agents 308b as described previously to lubricate the surface of the eye to promote epithelial and/or stromal healing.
 The post-treatment formulation(s) 308 may contain one or more glycosaminoglycans 308c, e.g., a nonsulfated glycosaminoglycan such as hyaluronic acid.
 The post-treatment formulation(s) 308 may be chilled to minimize edema of the stromal tissues.

The post-treatment formulation(s) 308 may contain one or more antibiotics 308d to prevent infection The post-treatment formulation(s) 308 may contain specialized polymers that remain on the eye for 24 hrs or more to act as a contact lens bandage.

The post-treatment formulation(s) 308 may be combined with currently available contact lens bandages or amniotic membrane ocular bandages.

The use of riboflavin as the cross-linking agent and UV light as the photo-activating light in the embodiments above is described for illustrative purposes only. In general, other types of cross-linking agents may be alternatively or additionally employed according to aspects of the present disclosure. Thus, for example Rose Bengal (4,5,6,7-tetrachloro-2',4',5',7'-tetraiodofluorescein) may be employed as a cross-linking agent. Rose Bengal has been approved for application to the eye as a stain to identify damage to conjunctival and corneal cells. However, Rose Bengal can also initiate cross-linking activity within corneal collagen to stabilize the corneal tissue and improve its biomechanical strength. Like Riboflavin, photoactivating light may be applied to initiate cross-linking activity by causing the Rose Bengal to general oxygen and/or other radicals in the corneal tissue. The photoactivating light may include, for example, UV light or green light. The photoactivating light, for instance, may include photons having energy levels sufficient to individually convert $O_2$ into singlet oxygen, or may include photons having energy levels sufficient to convert $O_2$ into singlet oxygen in combination with other photons, or any combination thereof.

Although embodiments of the present disclosure may describe stabilizing corneal structure after treatments, such as LASIK surgery, it is understood that aspects of the present disclosure are applicable in any context where it is advantageous to form a stable structure of corneal tissue through cross-linking. Furthermore, while aspects of the present disclosure are described in connection with the re-shaping and/or strengthening of corneal tissue via cross-linking the corneal collagen fibrils, it is specifically noted that the present disclosure is not limited to cross-linking corneal tissue, or even cross-linking of tissue. Aspects of the present disclosure apply generally to the controlled cross-linking of fibrous matter and optionally according to feedback information. The fibrous matter can be collagen fibrils such as found in tissue or can be another organic or inorganic material that is arranged, microscopically, as a plurality of fibrils with the ability to be reshaped by generating cross-links between the fibrils. Similarly, the present disclosure is not limited to a particular type of cross-linking agent or activating element, and it is understood that suitable cross-linking agents and activating elements can be selected according to the particular fibrous material being reshaped and/or strengthened by cross-linking. Furthermore, aspects of the present disclosure can be employed to monitor any type of photoactive marker and are not limited to cross-linking agents.

As described above, according to some aspects of the present disclosure, some or all of the steps of the above-described and illustrated procedures can be automated or guided under the control of a controller (e.g., the controller 120). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

What is claimed is:

1. A therapeutic combination for treating an eye, comprising:
   a formulation of riboflavin supplemented with oxygen, hydroxypropyl methylcellulose, one or more ionic surfactants, ethylenediaminetetraacetic acid (EDTA), a citrate;
   pulsed light illumination; and
   a mask configured to produce a consistent oxygen concentration above a surface of the eye.

2. The therapeutic combination of claim 1, wherein the one or more ionic surfactants comprises benzalkonium chloride.

3. The therapeutic combination of claim 1, wherein the pulsed light is pulsed Ultra Violet A light.

4. The therapeutic combination of claim 1, wherein the formulation further comprises one or more anesthetic agents.

5. The therapeutic combination of claim 4, wherein the one or more anesthetic agents is selected from the group consisting of pilocarpine, proparacaine, tetracaine, and oxybuprocaine.

6. The therapeutic combination of claim 1, wherein the formulation further comprises one or more analgesic agents.

7. The therapeutic combination of claim 6, wherein the one or more analgesic agents is selected from the group consisting of menthol, benzyl alcohol, and phenylethyl alcohol.

8. The therapeutic combination of claim 1, wherein the formulation further comprises one or more shear-thinning, viscosity-increasing agents.

9. The therapeutic combination of claim 8, wherein the one or more shear-thinning, viscosity-increasing agents is selected from the group consisting of carbomer, polycarbophil, gellan gum, and carboxymethyl cellulose sodium.

10. The therapeutic combination of claim 1, wherein the formulation further comprises one or more tonicity agents.

11. The therapeutic combination of claim 10, wherein the one or more tonicity agents is selected from the group consisting of glycerin, propylene glycol, polyethylene glycol (PEG)-8, ethanol, benzyl alcohol, phenylethyl alcohol, and triacetin.

12. The therapeutic combination of claim 1, wherein the mask includes an anterior side and a posterior side, the posterior side configured to be positioned proximate to the eye and the anterior side configured to be positioned distally from the eye.

13. The therapeutic combination of claim 12, wherein the mask includes an outer wall extending at least between the anterior side and the posterior side.

14. The therapeutic combination of claim 13, wherein the mask further comprises a transmission region configured to allow a pulsed light to be delivered to the eye.

15. The therapeutic combination of claim 14, wherein the pulsed light is pulsed Ultra Violet A light.

16. The therapeutic combination of claim 12, wherein the mask further comprises an oxygen delivery system.

17. The therapeutic combination of claim 16, wherein the mask comprises a diffuser configured to deliver the oxygen above the surface of the eye.

18. The therapeutic combination of claim 17, wherein the oxygen concentration above the surface of the eye is greater than a concentration of oxygen in ambient air.

* * * * *